(12) United States Patent
Gysling

(10) Patent No.: US 12,123,889 B2
(45) Date of Patent: Oct. 22, 2024

(54) APPARATUS AND METHOD FOR MEASURING A PARAMETER OF A PROCESS FLUID

(71) Applicant: Corvera, LLC, South Glastonbury, CT (US)

(72) Inventor: Daniel Gysling, South Glastonbury, CT (US)

(*) Notice: Subject to any disclaimer, the term of this patent is extended or adjusted under 35 U.S.C. 154(b) by 0 days.

(21) Appl. No.: 18/579,440

(22) PCT Filed: Dec. 15, 2022

(86) PCT No.: PCT/US2022/052985
§ 371 (c)(1),
(2) Date: Jan. 15, 2024

(87) PCT Pub. No.: WO2023/114382
PCT Pub. Date: Jun. 22, 2023

(65) Prior Publication Data
US 2024/0264061 A1    Aug. 8, 2024

Related U.S. Application Data

(60) Provisional application No. 63/358,969, filed on Jul. 7, 2022, provisional application No. 63/366,243, filed
(Continued)

(51) Int. Cl.
*G01N 9/00* (2006.01)
*G01F 1/66* (2022.01)
*G01N 9/24* (2006.01)

(52) U.S. Cl.
CPC ............... *G01N 9/002* (2013.01); *G01F 1/66* (2013.01); *G01N 9/24* (2013.01); *G01N 2009/006* (2013.01)

(58) Field of Classification Search
CPC .... G01N 9/002; G01N 9/24; G01N 2009/006; G01F 1/66
See application file for complete search history.

(56) References Cited

U.S. PATENT DOCUMENTS

| | | |
|---|---|---|
| 5,600,073 A | 2/1997 | Hill |
| 2003/0154036 A1* | 8/2003 | Gysling ............... G01F 1/666 702/25 |

(Continued)

*Primary Examiner* — Tarun Sinha
(74) *Attorney, Agent, or Firm* — Matthew J Patterson

(57) ABSTRACT

A method is disclosed including providing a process fluid that can be described as having a plurality of components where each of the plurality of components has a respective mass fraction. In addition, the method includes providing an initial estimate of a compositional description for the plurality of components of the process fluid, measuring an ultrasonic sound speed of the process fluid, predicting a predicted sound speed of a liquid phase of the process fluid using an equation of state model, generating an error function using the ultrasonic sound speed of the process fluid and the predicted sound speed of a liquid phase of the process fluid, minimizing the error function and updating the respective mass fractions of the plurality of components and determining an optimized compositional description of the process fluid. Also disclosed are corresponding computer systems, apparatus, and computer programs configured to perform the actions of the methods.

22 Claims, 11 Drawing Sheets

Related U.S. Application Data on Jun. 11, 2022, provisional application No. 63/328,410, filed on Apr. 7, 2022.

(56) References Cited

U.S. PATENT DOCUMENTS

| | | | |
|---|---|---|---|
| 2005/0044929 A1* | 3/2005 | Gysling | G01F 1/8477 73/32 A |
| 2005/0081643 A1 | 4/2005 | Mattar | |
| 2008/0053240 A1 | 3/2008 | Henry | |

* cited by examiner

APPARATUS AND METHOD FOR MEASURING A PARAMETER OF A PROCESS FLUID

CROSS REFERENCE TO RELATED APPLICATIONS

This application claims the benefit of U.S. Provisional Patent Application Ser. No. 63/265,610 filed 17 Dec. 2021, U.S. Provisional Application Ser. No. 63/328,410 filed 7 Apr. 2022, U.S. Provisional Patent Application Ser. No. 63/358,969 filed 7 Jul. 2022, as well as Patent Cooperation Treaty Patent Application Serial No. PCT/US2022/052985 filed on 15 Dec. 2022. The disclosures of the applications above are incorporated herein by reference in their entirety.

BACKGROUND

Field of Disclosure

The present disclosure relates to methods and apparatus for measuring bubbly flows of liquids at or near their transition point.

Description of the Related Art

There is a need to measure the mass flow, density, and volumetric flow of fluids that are at or near phase transition boundaries. Examples of this include Liquefied Natural Gas (LNG), Liquefied Petroleum Gas (LPG), and Carbon Dioxide ($CO_2$). Each fluid is transported and/or processed at or near phase transition boundaries. The physical properties, such as liquid and gas phase sound speed and density, of fluids operating near phase transition boundaries LNG can vary significantly with small changes in the pressure and temperature and composition of the fluid. Additionally, while estimates of the composition of such fluid generally exist, the variability of properties of the gas and liquid phases near phase transitions drive a need to for real time determination of the properties of the gas and liquid phases required to perform accurate measurement.

If any gaseous phase is not present, it is important to accurately measure the flow rate and to provide information on the composition of the fluid. Implementations of the current disclosure utilize Liquefied Natural Gas (LNG) as an example, however, the discussion of the flow measurement challenges in measuring LNG are applicable to any fluid which is operating near phase transition boundaries and this disclosure is not so limiting.

Measuring LNG poses many challenges for conventional flow meters. Most flow meters measure volumetric flow, however, LNG typically is measured on a mass flow basis, and often by Coriolis flow meters. LNG is natural gas comprised of various components that is cooled until the gaseous phase condenses into a liquid. If the liquid is cooled to below its boiling point, it is termed a sub-cooled liquid. For methane, typically the dominate component of LNG, the condensation temperature at ambient pressure is approximately 113 K or −160 C, or ~−250F. The liquefied gas has a density on the order of 600 times the density of the gaseous form at ambient pressure. The natural gas can be more easily transported in this cooled, liquefied state.

While in this liquefied state, the pressure of the LNG is often maintained at or near ambient pressure, allowing transport of the LNG in non-pressurized containers. As the LNG absorbs heat during transport, the temperature of liquid phase of the LNG is maintained at the boiling temperature, or vapor transition point, by allowing a portion of the LNG to "boil-off". Since the LNG is transferred essentially at its boiling point, gas breakout of the vapor phase from the liquid phase is often encountered during product transfer and other conditions in which the mass flow rate of the product is sought.

LNG is often transported in thermally insulated, non-pressurized vessels with the LNG existing near it's boiling temperature. Heat is absorbed by the liquefied natural gas, some of liquid boils off, allowing the remaining liquid to remain a liquid, albeit at conditions very close to it boiling point. The gas that boils off is typically collected, and either used as fuel for the vessel, or re-condensed into a cryogenic liquid and reintroduced into the vessel.

Coriolis flow meters of the prior art are not, in general, well-suited for measuring LNG if gas, in its vapor phase, is present. The composition of the LNG, i.e. percentage of methane, ethane, and propane, etc., can vary from batch to batch, often depending on the source of the LNG. Additionally, the composition within a single batch can varying during transfer due to settling of heavier components and outgassing of lighter components due to boil off cooling. Variations in composition result in changes in boil points and variations in liquid and vapor phase properties as a function of pressure and temperature.

All these challenges make accurate, dynamic, fiscal measurement of LNG difficult. What is needed is an accurate method to measure LNG that is insensitive to outgassing to effectively measure the characteristics of LNG at or near it boiling point.

In certain processes, transportation and manufacturing environments, the phase transition boundaries are important from a flow measurement perspective. If the fluid is at or near a liquid (or dense phase) to gaseous phase transition boundary, there is a need determine if any gaseous phase is present, and if a gas phase is present, there is a need to quantify the amount of gas present and to correct for the effects of the gaseous phase on the flow measurement.

SUMMARY

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

In one general aspect, a method may include providing a process fluid having a plurality of components where each of the plurality of components has a respective mass fraction. The method may also include providing an initial estimate of a compositional description for the plurality of components of the process fluid. The method may furthermore include measuring an ultrasonic sound speed of the process fluid. The method may in addition include predicting a predicted sound speed of a liquid phase of the process fluid using an equation of state model. The method may moreover include generating an error function using the ultrasonic sound speed of the process fluid and the predicted sound speed of a liquid phase of the process fluid. The method may also include minimizing the error function and updating the respective mass fractions of the plurality of components. The method may furthermore include determining an optimized compositional description of the process fluid. Other embodiments of this aspect include corresponding computer systems, apparatus, and computer programs recorded on one or more computer storage devices, each configured to perform the actions of the methods.

Implementations may include one or more of the following features. The method may include determining a liquid phase density of the process fluid. The method where the process fluid is proximate a phase transition boundary. The method may include measuring an acoustic speed of sound of the process fluid. The method may include determining a gas void fraction of the process fluid. The method may include providing a Coriolis meter, measuring a measured density of the process fluid with the Coriolis meter, measuring a mass flow of the process fluid with the Coriolis meter, and determining any of a corrected density of the process fluid and a corrected mass flow of the process fluid using any of the gas void fraction and the liquid phase density. The method may include positioning a first acoustic pressure sensor proximate an inlet portion of the Coriolis meter and positioning a second acoustic pressure sensor proximate an outlet portion of the Coriolis meter, measuring the acoustic sound speed of the process fluid using the first acoustic pressure sensor and the second acoustic pressure sensor, positioning a normal incident ultrasonic sensor on a conduit positioned proximate the outlet portion of the Coriolis meter, and measuring the ultrasonic sound speed of the process fluid using the normal incident ultrasonic sensor. The method where measuring an acoustic speed of sound of the process fluid may include measuring frequencies in the range less than 20 kilohertz. The method may include predicting at least one parameter of the process fluid using the optimized compositional description of the process fluid. The method may include predicting at least one fluid property for a vapor phase of the process using the optimized compositional description of the process fluid. The method where the measuring an ultrasonic sound speed of the process fluid may include measuring frequencies in the range above 20 kilohertz. Implementations of the described techniques may include hardware, a method or process, or a computer tangible medium.

In one general aspect, a system having a process fluid having a plurality of components where each of the plurality of components has a respective mass fraction may include one or more processors configured to provide an initial estimate of a compositional description for the plurality of components of the process fluid, measure an ultrasonic sound speed of the process fluid, predict a predicted sound speed of a liquid phase of the process fluid using an equation of state model, generate an error function using the ultrasonic sound speed of the process fluid and the predicted sound speed of a liquid phase of the process fluid, minimize the error function and updating the respective mass fractions of the plurality of components, and determine an optimized compositional description of the process fluid. Other embodiments of this aspect include corresponding computer systems, apparatus, and computer programs recorded on one or more computer storage devices, each configured to perform the actions of the methods.

Implementations may include one or more of the following features. The systems further configured to determine a liquid phase density of the process fluid. The systems where the process fluid is proximate a phase transition boundary. The systems further configured to measure an acoustic speed of sound of the process fluid. The systems further configured to determine a gas void fraction of the process fluid. The systems may include a Coriolis meter configured to measure a measured density of the process fluid, measure a mass flow of the process fluid, and where the one or more processors is further configured to determine any of a corrected density of the process fluid and a corrected mass flow of the process fluid using any of the gas void fraction and the liquid phase density. The systems may include a first acoustic pressure sensor positioned proximate an inlet portion of the Coriolis meter and a second acoustic pressure sensor positioned proximate an outlet portion of the Coriolis meter, a conduit positioned proximate the outlet portion of the Coriolis meter, a normal incident ultrasonic sensor positioned on the conduit, and where the one or more processors is further configured to determine the ultrasonic sound speed of the process fluid using the normal incident ultrasonic sensor and to determine the acoustic sound speed of the process fluid using the first acoustic pressure sensor and the second acoustic pressure sensor. The systems where measuring an acoustic speed of sound of the process fluid may include measuring frequencies in the range less than 20 kilohertz. The systems may include predicting at least one parameter of the process fluid using the optimized compositional description of the process fluid. The systems may include predicting at least one fluid property for a vapor phase of the process using the optimized compositional description of the process fluid. The systems where the measuring an ultrasonic sound speed of the process fluid may include measuring frequencies in the range greater than 20 kilohertz. Implementations of the described techniques may include hardware, a method or process, or a computer tangible medium.

BRIEF DESCRIPTION OF THE DRAWINGS

So that the manner in which the above-recited features of the present disclosure can be understood in detail, a more particular description of the disclosure, briefly summarized above, may be had by reference to implementations, some of which are illustrated in the appended drawings. It is to be noted, however, that the appended drawings illustrate only typical implementations of this disclosure and are therefore not to be considered limiting of its scope, for the disclosure may admit to other equally effective implementations.

DETAILED DESCRIPTION

In the following detailed description, reference is made to the accompanying drawings, which form a part hereof, and within which are shown by way of illustration specific implementations by which the examples described herein may be practiced. It is to be understood that other implementations may be utilized and structural changes may be made without departing from the scope of the disclosure.

Implementations of the present disclosure provide systems and methods to measure the mass flow, density, and volumetric flow of fluids that are at or near phase transition boundaries. Implementations include methods of augmenting Coriolis meters with a sub-bubble resonant sound speed measurement and a super-bubble resonant sound speed measurement. As will be disclosed herein after, these two additional sound speed measurements enable accurate measurement of the mass flow and density of fluids with entrained gases and fluids with highly uncertain and/or variable vapor phase properties and variable liquid phase properties, such as fluids in a predominately liquid state at, or near, their boiling points, such as LNG.

The speed of sound of a fluid is a physical property of the mixture. Fluids can be gases or liquids, or mixtures of gases and liquids. For bubbly mixtures the speed of sound has at least two distinct frequency regimes, each of which provide different information of the fluid. The two frequency regimes are divided by the resonant frequency of the bubbles as set forth in U.S. Pat. No. 7,526,966 and in Temkin reference Referring to FIG. 1, there is shown the liquid phase sound speed divided by mixture sound speed for a bubbly mixture as a function of frequency from the prior art. The frequency is nondimensionalized by the bubble resonant frequency, defined as the natural frequency of the "radial" resonance of the bubbly, i.e. a radially symmetric oscillation of the volume of the bubble. This natural frequency is given by Minnaert's equation (Equation 1):

$$\omega_0 = \frac{c_{gas}}{R_o} \sqrt{3 \frac{\rho_{gas}}{\rho_{liq}}} \quad \text{(Equation 1)}$$

Where $R_o$ is the mean radius of the oscillating bubble, $c_{gas}$ is the speed of sound in the gas contained in the bubble, and $\rho_{gas}$ and $\rho_{liq}$ are the ambient densities of the gas and of the liquid, respectively.

Figure 1:
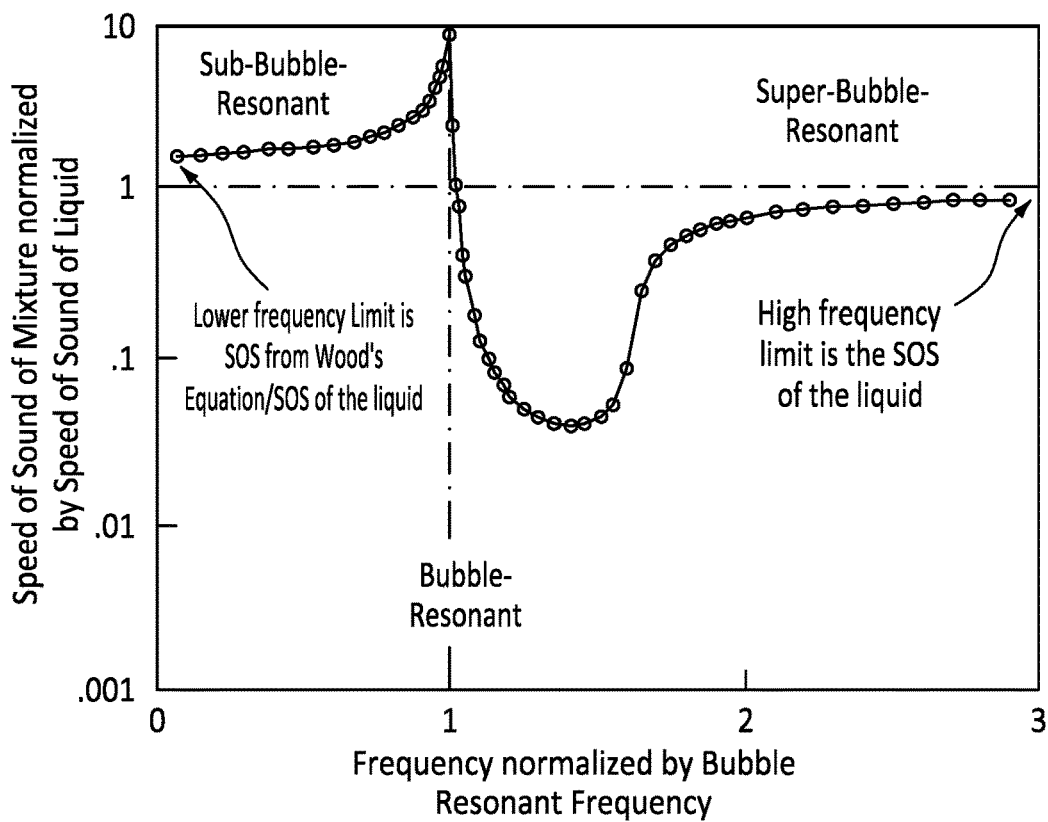
FIG. 1 is a graphical representation of the liquid phase sound speed divided by mixture sound speed for a bubbly mixture as a function of frequency from the prior art.

FIG. 1, shows a graphical representation of the speed of sound of a bubbly mixture. In the Figure, the speed of sound in the liquid phase of a mixture is divided by the speed of sound of the mixture and plotted as a function of frequency, normalized by the bubble resonant frequency for an air and water mixture at ambient pressure and temperature with a gas void fraction of 0.0001 (or 0.01%) of the prior art. As shown, the sound speed of the mixture for frequencies below and above the bubble resonant frequency asymptote to different values. These two values to which the sound speed asymptotically approaches are defined as the sub-bubble-resonant and super-bubble-resonant sound speeds, respectively.

One method to measure the sub-bubble-resonant speed of sound utilizes an array of pressure sensors distributed axially along a flow conduit. One method to measured the super-bubble-resonant sound speed utilizes ultrasonic sensors that transmit and detect the speed at which high frequency sound propagates through the mixture. As is known in the art, and as used as part of this disclosure, measuring the speed of sound in the ultrasonic frequency range includes frequencies from 20 kHz up to several megahertz.

Figure 2:
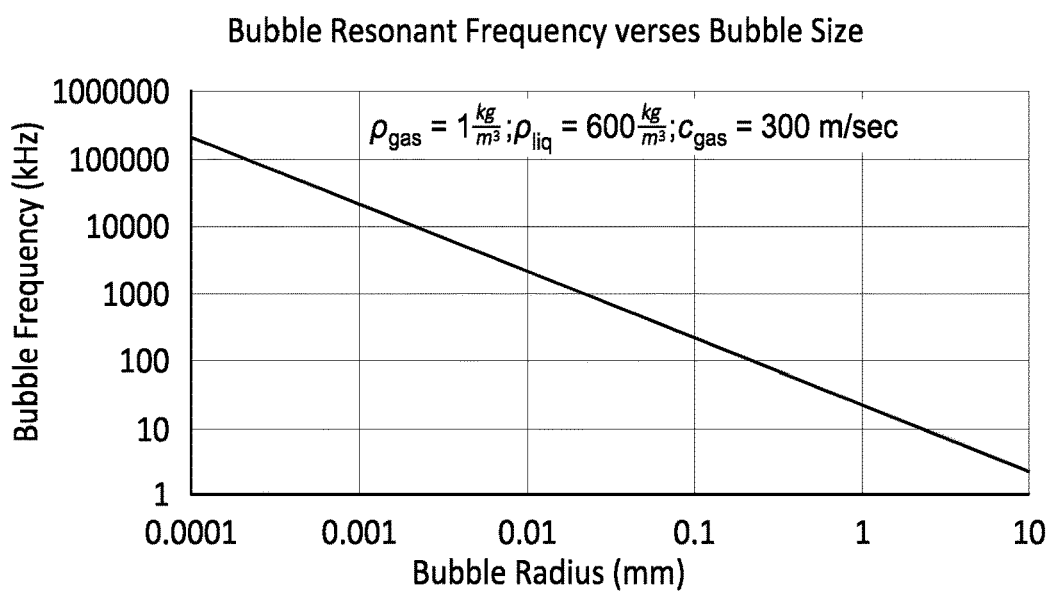
FIG. 2 is a graphical representation of the bubble resonant frequency versus bubble radius for a representative bubbly mixture from the prior art.

Referring to FIG. 2, shown is the resonate bubble frequency (in kHz) (as defined by Equation 1) versus bubble radius (in mm) for a representative gas and liquid mixture. As shown, the minimum frequency required to determine the super-bubble-resonant sound speed scales inversely with bubble size. In this example, a 1000 kHz (1 mHz) ultrasonic transducer would be suitable for determining the super-bubble resonant sound speed for mixtures for which the mean bubble size was greater than ~0.1 mm. In general, for mixtures with smaller bubble sizes, higher frequency ultrasonic transducers would be required to measure the super-bubble resonant sound speed. Measuring the sub-bubble-resonant speed sound requires utilizing frequencies well-below the bubble resonant frequencies, and frequencies for which the wavelength of the sound is significantly larger than the cross sectional dimension of the conduit conveying the process fluid, ie the diameter of a circular cross section conduit.

As will be disclosed in more detail herein after, these sound speed measurements, when integrated within a Coriolis meter, and combined with the fundamental measurements provided by a standard Coriolis meter, namely a mass flow measurement derived from a measured phase lag indicative of a deformation in the vibratory mode shape of the process-fluid conveying flow tubes in a Coriolis meter caused by the mass flow though the vibrating flow tube, and a process fluid density measurement derived from a measured natural frequency of a vibrating process-fluid conveying flow tubes, provide the basis for a practical, accurate, robust method to measure fluids at or near phase transition boundaries such as LNG or CO2.

The methods disclosed herein provide a means to improve the mass flow measurement, but also, provide a means to improve the density measurement of the liquid phase, and a means to improve knowledge of the composition of the fluid. The improved knowledge of the composition can be used, for example, to determine the energy content of an LNG mixture, or, for another application, the level of impurities in a CO2 mixture.

The methodology disclosed herein has many advantages over the current state of the art for measuring bubbly fluids with highly variable liquid and vapor phase properties. Currently, conventional Coriolis meters provide mass flow measurement that is based on calibrations developed for homogeneous flows at low or negligible reduced frequencies. The energy content of quantify of LNG is typically determined by multiplying the total mass, as determined by integrating a mass flow rate measure over time, with an estimate, or measurement, of the energy content per unit mass. However, in cases where a gaseous phase may be present, this approach will result in errors in the reported mass flow and density reported from the Coriolis meter due to the bubbly flow conditions within the Coriolis meter, thereby impairing the ability to provide an accurate estimate of the energy content of the LNG.

It is well known that the introduction of entrained gas in liquids can result in errors in the reported mass flow and density from Coriolis meters (Hemp, 2006). Coriolis meters are typically calibrated on homogeneous fluids at low reduced frequencies. Using these calibrations, which are based on homogenous flows, typically results in errors in the reported mass flow and density from Coriolis meter operating on multiphase process fluids.

One of the challenges of measuring LNG is the high variability of the sound speed and densities of the liquid and vapor phases under conditions at which LNG is often measured, i.e. near or within phase transition boundaries. Table 1 shows the composition in terms of mass fraction of components of a natural gas representative of that a gas produced in from a well and is used as an example of a natural gas as part of the current disclosure.

TABLE 1

| Component | Mass fraction (%) |
|---|---|
| Methane | 73.4 |
| Nitrogen | 1.5 |
| CO2 | 3.5 |
| Ethane | 13.6 |
| Propane | 5.4 |
| Butane | 1.1 |
| Isopentane | 1.1 |
| Pentane | 0.2 |
| Hexane | 0.2 |

The relative percentage of the mass fractions of the various compositional components can be adjusted to update the predicted vapor and liquid properties from the equation of state models used within commonly available PVT software that generate estimates of the thermophysical properties of mixtures based as a function of thermodynamic state variables such as pressure and temperature based on a description of the mass fractions of the constituents of various components.

Figure 3:
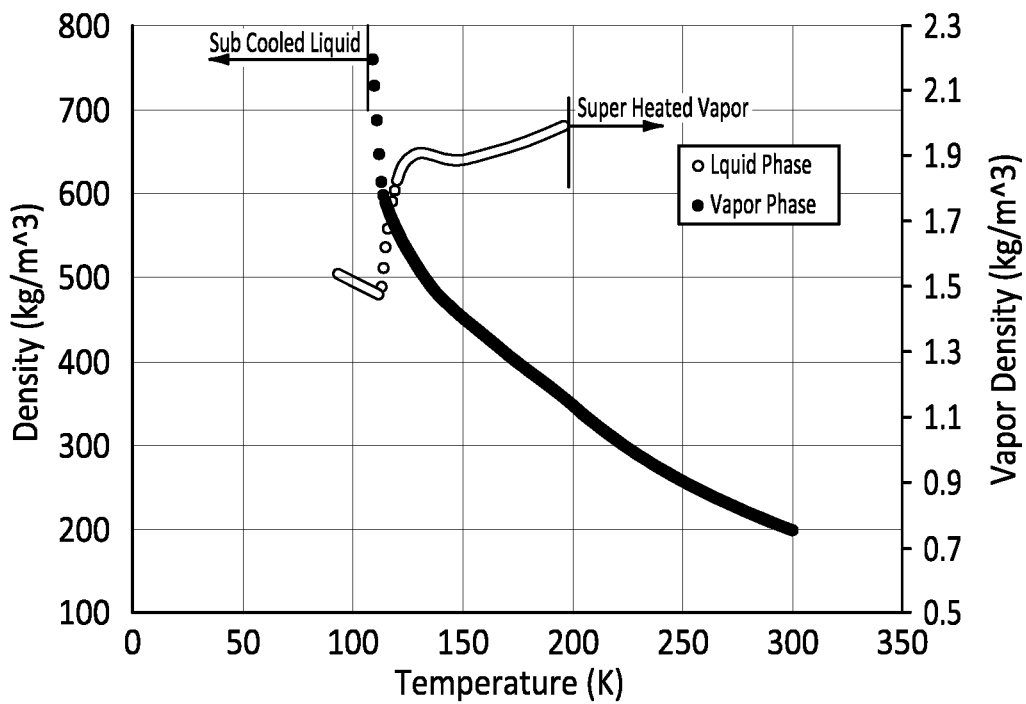
FIG. 3 is a graphical representation of the densities of the liquid and vapor phases at 1 atm for a representative natural gas composition from the prior art.
Figure 4:
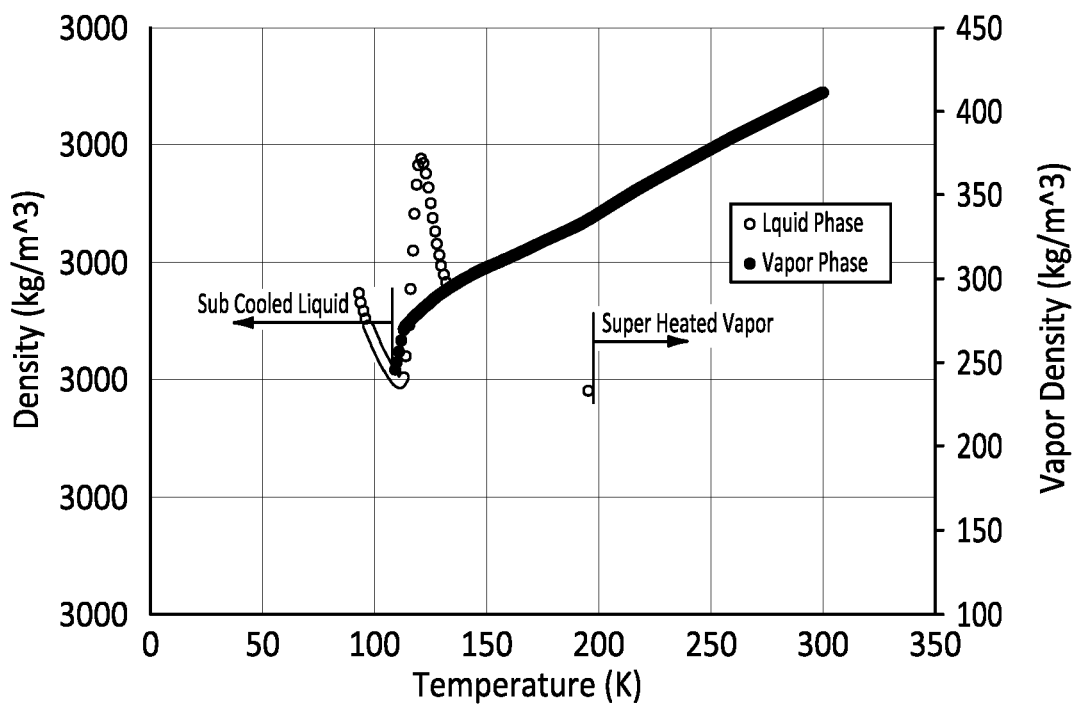
FIG. 4 is a graphical representation of the speed of sound of the vapor and liquid phases of a representative natural gas as a function of temperature at 1 atmosphere from the prior art.

Referring now to FIG. 3, there is shown the density of the vapor and liquid phases of a representative LNG mixture predicted using a commercially available compositionally based equation of state model as a function of temperature at 1 atmosphere. The term Equation of State (EoS) model used herein is defined as a mathematical model that enables the calculation of thermodynamic properties (such as density of liquid phase and speed of sound of liquid phase) and equilibria between liquid and vapor phases (such as bubble point) of a process fluid, consisting of a mixture or one or more pure substances, as a function of the temperature, pressure and composition of the process fluid. Such an equation of state model can be found in Reference Fluid Thermodynamic and Transport Properties Database (REF-PROPS), a software program developed by the National Institute of Standards and Technology (NIST), which calculates the thermodynamic and transport properties of industrially important fluids and their mixtures (https://www.nist-.gov/programs-projects/reference-fluid-thermodynamic-and-transport-properties-database-refprop). As shown, the density of the liquid and vapor phases are highly variable with process temperature. Note that the plot of FIG. 3, shows the variation only due to temperature, however, the density is also highly variable with compositional changes, as well as with pressure changes at/or near the boiling point. The plot of FIG. 4 shows the speed of sound of the vapor and liquid phases of a representative natural gas composition as a function of temperature at 1 atmosphere. As shown, like the densities of FIG. 3, the sound speeds of the components are highly variable near the phase transition boundary.

Figure 5:
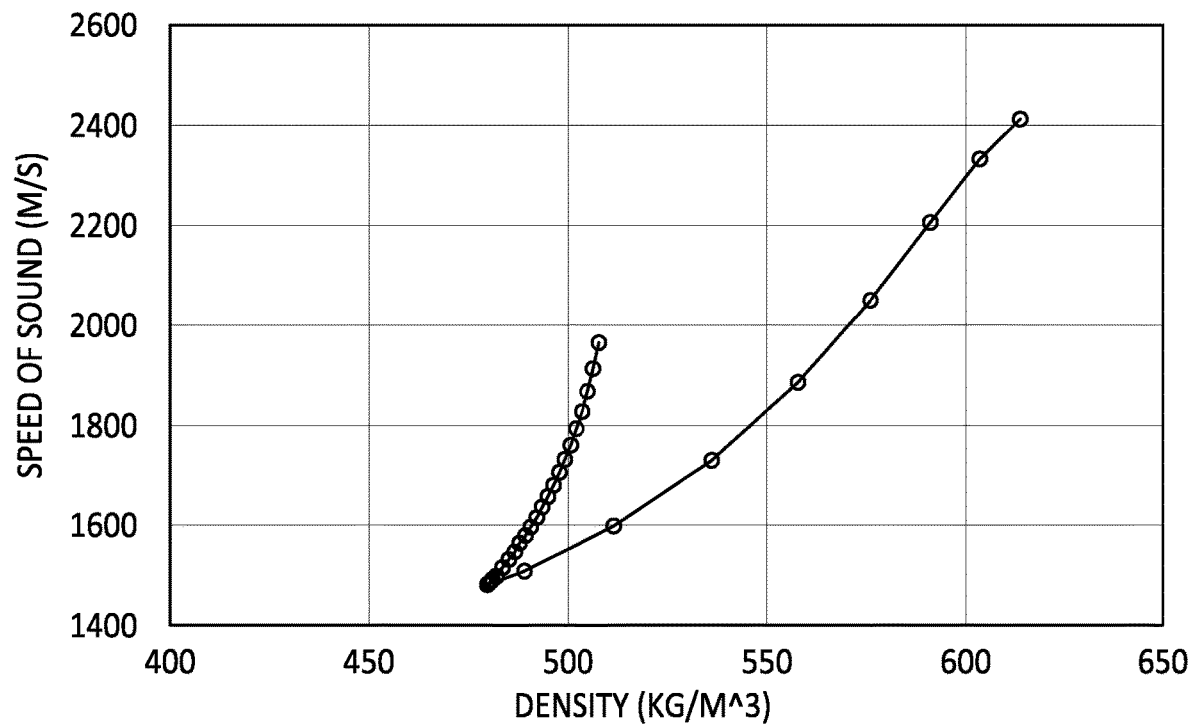
FIG. 5 is a graphical representation of the liquid phase sound speed versus density for constant pressure, varying temperature near bubble point in accordance with the present disclosure.

Referring next to FIG. 5, the plot shows the predicted sound speed of the liquid phase plotted versus the density of the liquid phase near the mixture's boiling point over a range of temperatures for the natural gas of Table 1. As shown, the behavior of the speed of sound versus density changes qualitatively at the bubbly point, with both sound speed and density decreasing with increasing pressure for temperatures below the boiling point, and both the sound speed and the density of the liquid phase increasing with temperature for temperatures above the boiling point of the mixture. This behavior of the sound speed and density of the liquid phase at temperatures above the boiling point of the original mixture can be attributed to the composition of the liquid phase changing due to the lighter molecules boiling off from the liquid phase at temperatures above the boiling point of the original sub-cooled LNG liquid.

Figure 6:
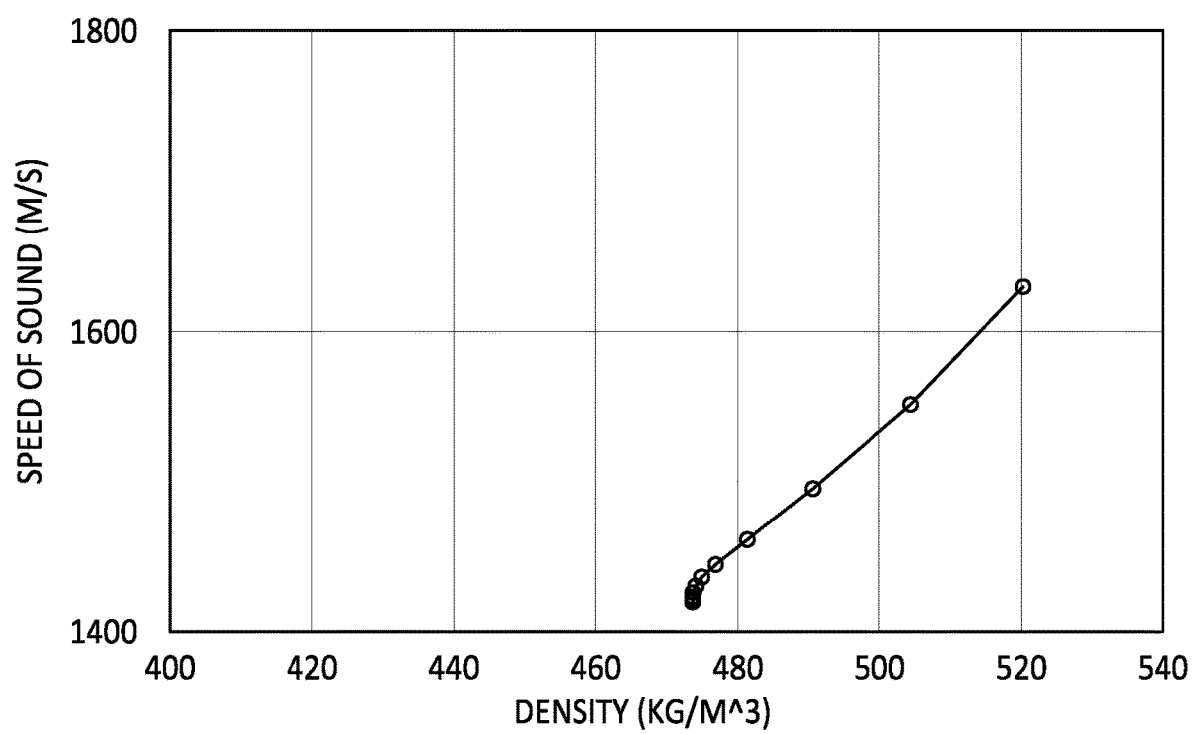
FIG. 6 is a graphical representation of the liquid phase sound speed versus density for constant temperature, varying pressure near bubble point in accordance with the present disclosure.

With reference to FIG. 6, the plot shows the speed of sound of the liquid phase versus the density of the liquid phase for a LNG mixture at a constant temperature, but varying pressure. As shown, as the pressure decreases below the boiling the point for this temperature, both the density and the sound speed of the liquid phase increase.

Implementations of the current disclosure includes methods of utilizing a sub-bubble resonant sound speed measurement and a super-bubble resonant sound speed measurement and a Coriolis flow meter, along with measured process pressure and temperature, and an equation of state model for the process fluid to estimate the properties of the liquid and the vapor phase of the fluid as well as provide improved measurement of the mass flow, density, and gas void fraction of a fluid at or near it's phase transition point, such as LNG at or near its boiling point.

As will be disclosed in more detail herein below, determining liquid and vapor properties and the vapor void fraction (i.e. the gas void fraction) enables implementations of methods used to correct the mass flow and density measurements from Coriolis meter operating on the bubbly mixtures, particularly when the bubbly mixture is a fluid at or near phase transition boundaries.

Figure 7:
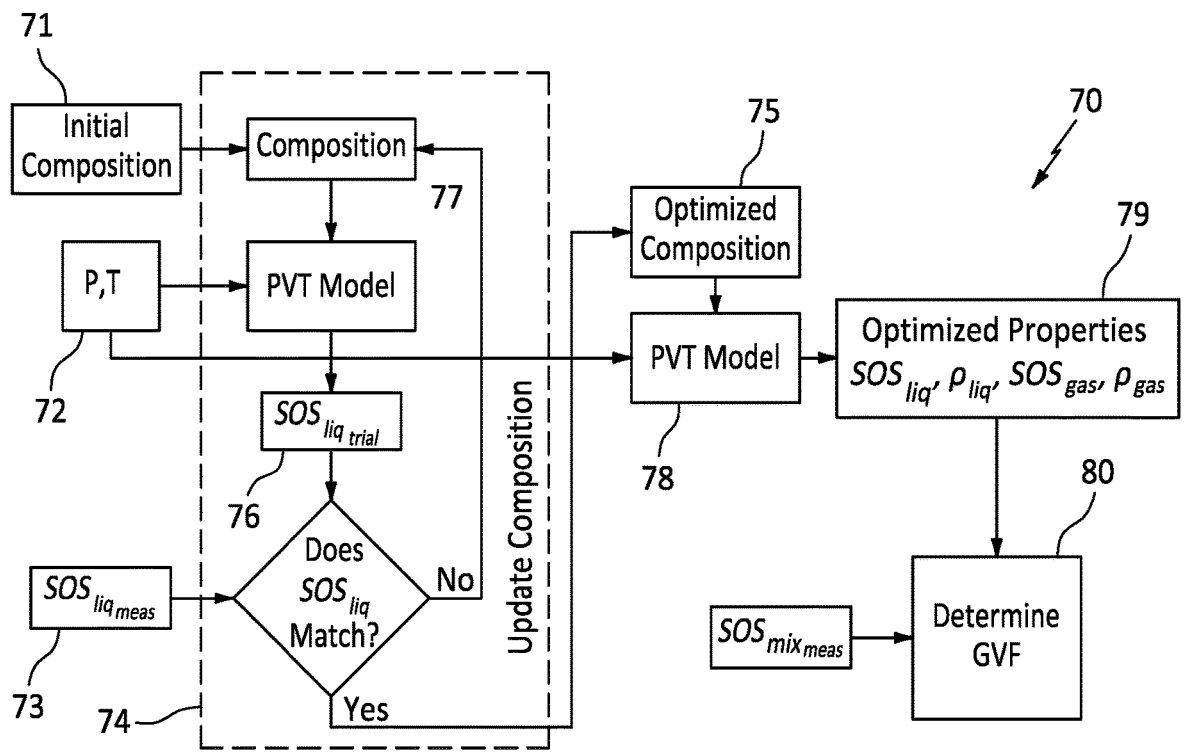
FIG. 7 is a schematic representation of a method to determine gas void fraction of a bubbly fluid in accordance with the present disclosure.

Referring next to FIG. 7, there is shown a schematic of a method 70 to utilize inputs of the initial composition of a bubbly fluid 71, the measure pressure and temperature of the gas 72 and the measured super-bubble resonate sound speed 73 in an error function 74 using an iterative process to determine an optimized fluid composition 75 for a bubbly fluid by minimizing the error between the measured liquid phase sound speed and the liquid phase sound speed 76 predicted by a PVT model 77. The PVT model 78 (which can be the same as PVT model 77) with the optimized composition 75 is then used to generate the fluid properties of the liquid and vapor phases at the measured pressure and temperature 79. These fluid properties are then used as input to Wood's equation, or a functionally similar model, which relates the measured sub-bubble resonant sound speed to the gas void fraction of the mixture to determine the gas void fraction 80 of the mixture. As shown, this methodology provides a means to determine liquid density and the gas void fraction a process fluid utilizing an PVT model of a fluid near phase transition boundaries. There are many potential implementations of methods of the current disclosure which leverage various numerical models and assumptions that utilize some or all of the following 1) a measured sub-bubble resonant sound speed; 2) a measured super-bubble-resonant sound speed; 3) a model for the thermophysical properties of a fluid; and 4) a model that relates the sub-bubble-resonant sound speed to the properties of the gas and the liquid phases, to determine the gas void fraction of a bubbly mixture and the density of the liquid phase. The determined gas void fraction 80, and the optimized value for the density of the liquid phase 79, can then be used, in models to correct the mass flow and or density measured by a Coriolis meter for errors—associated with the Coriolis meter operating on a bubbly flow.

Figure 8:
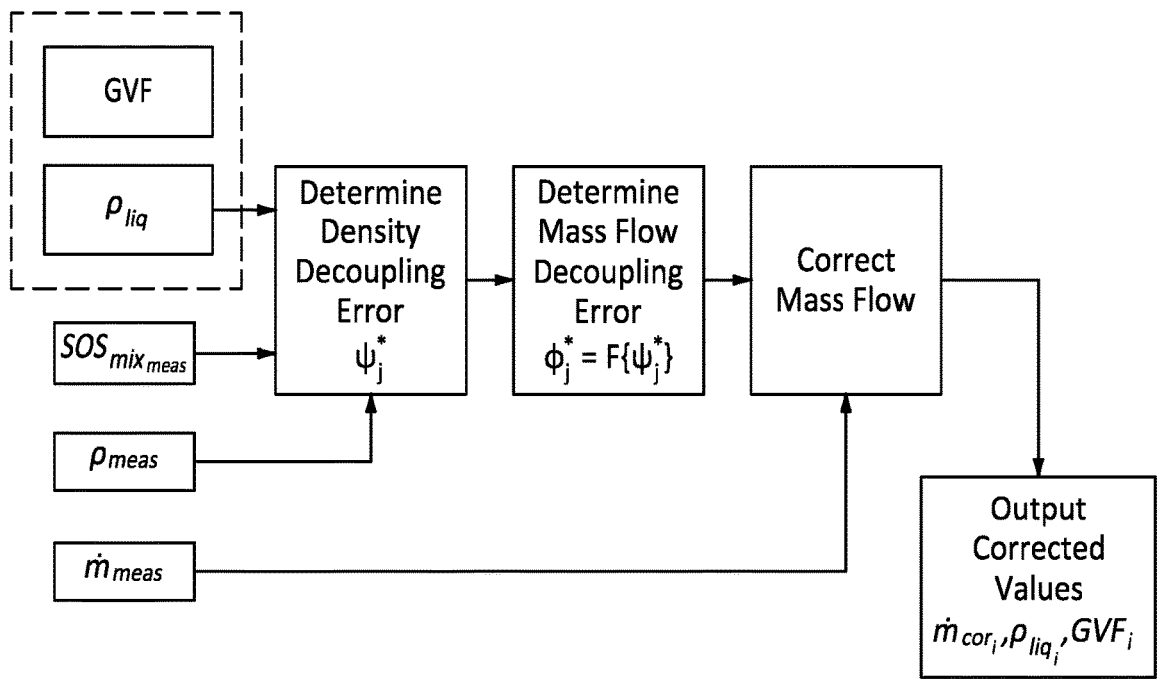
FIG. 8 is a schematic representation of a method to correct mass flow, density, and gas void fraction from a Coriolis meter operating on fluid near phase transition point in accordance with the present disclosure.

One such method that utilizes a measurement of the process fluid sub-bubble resonant sound speed, the gas (or vapor) void fraction, and knowledge of the density of the liquid phase to correct the output of a Coriolis meter is described in U.S. Provisional Patent Application Ser. No. 63/358,969 (the '969 application) having a filing date of 7 Jul. 2022 titled "Optimization of Correlation between Mass Flow Decoupling Error and Density Decoupling Error" the disclosure of which is included herein by reference in its entirety. Referring to FIG. 8, there is shown a schematic of how methods of the current disclosure can be used to determine the gas void fraction and liquid phase density of a fluid at or near phase transition boundaries to measure the mass flow, density, and vapor (gas) void fraction of a bubbly fluid combined with Equation 2 and Equation 3 below.

The method shown in FIG. 8 is disclosed in more detail below as well as in the '969 application, can advantageously utilize the gas void fraction and liquid phase density determined using the methods described above. The determined liquid phase density is used with density measured from the Coriolis meter (as interpreted by the Coriolis meter utilizing a calibration developed for homogeneous fluid operating at a low reduced frequency) and the sub-bubble-resonant speed of sound measurement to determine a density decoupling error term $\Psi^*$ defined as:

$$\Psi^* \equiv 1 - \frac{\rho_{meas}}{\rho_{liq}} + G_d(f_{red})^2 \quad \text{(Equation 2)}$$

Where $$f_{red} \equiv \frac{2\pi f_{tube} D/2}{a_{mix}}$$

is the reduced frequency, and $G_d$ is an empirically determined density compressibility error coefficient.

The density decoupling error term $\Psi^*$ can be correlated to a similarly defined mass flow decoupling error term $\Phi^*$ defined as follows:

$$\Phi^* \equiv 1 - (1-\alpha)\left\{ \frac{\dot{m}_{meas}}{\dot{m}_{liq}} + G_m(f_{red})^2 \right\} \quad \text{(Equation 3)}$$

Where $G_m$ is an empirically determined mass flow compressibility error coefficient.

As defined, the density decoupling error function of Equation 2 and the mass flow decoupling error function of Equation 3 contain measured and reference values as well as the mass flow and density compressibility error coefficients, $G_m$ and $G_d$. It should be appreciated by those skilled in the art that, as part of the present disclosure, this disclosure teaches a preferred method to determine optimized values for the compressibility error coefficients ($G_m$ and $G_d$) for a given Coriolis meter operating over a given range of operating parameters.

Figure 9:
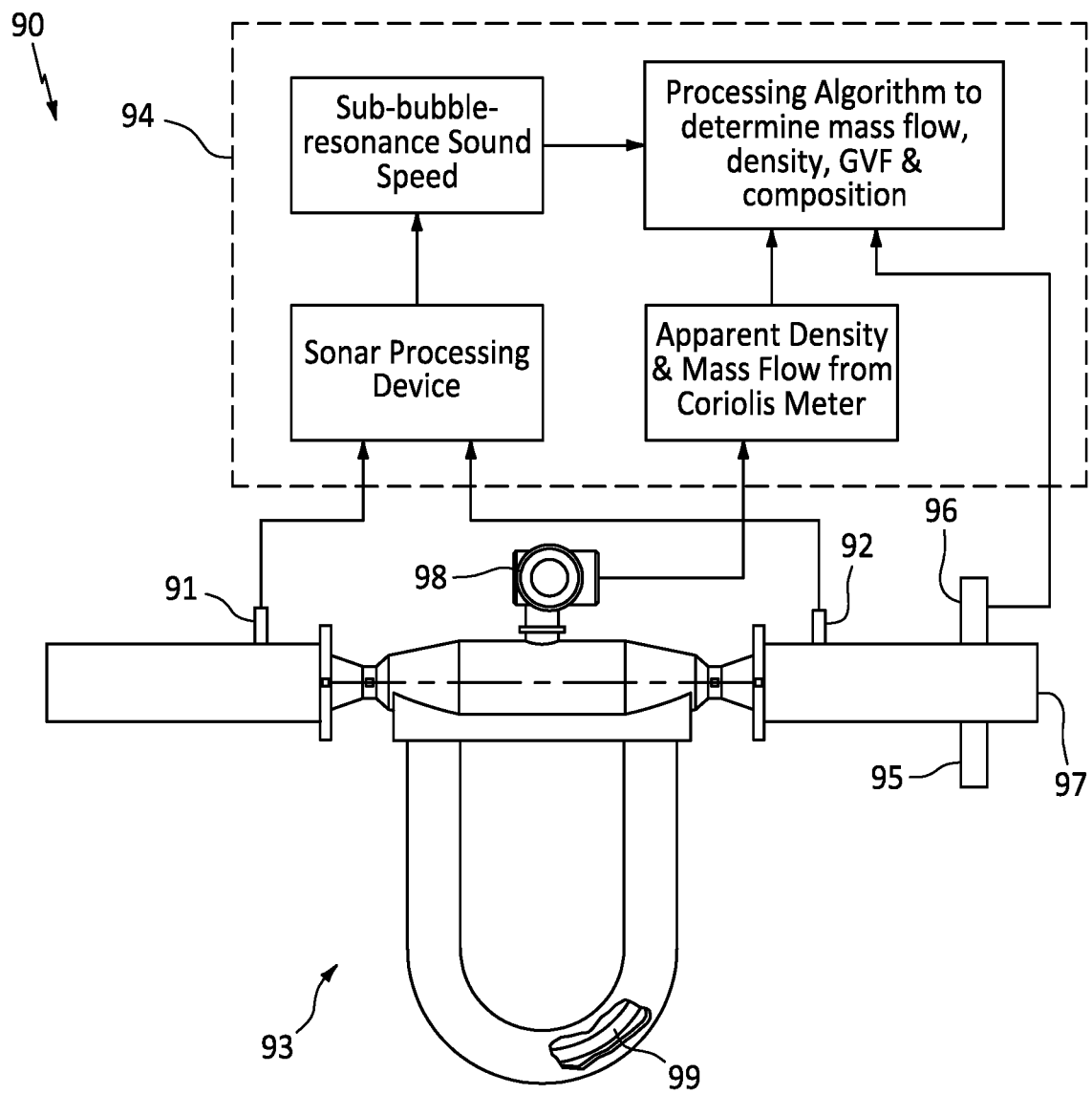
FIG. 9 is a schematic representation of a sub-bubble-resonant and super-bubble-resonant speed of sound augmented Coriolis meter in accordance with the present disclosure.

Referring to FIG. 9, there is shown a schematic of an implementation of a sub-bubble-resonant and super-bubble-resonant speed of sound augmented Coriolis meter 90 in accordance with the current disclosure. The augmented Coriolis meter 90 utilizes an array of ported pressure transducers including first pressure transducer 91 positioned proximate an inlet portion of the Coriolis meter and second pressure transducer 92 positioned proximate an outlet portion of the Coriolis meter such that the pressure transducers span the flow tubes 99 of Coriolis meter 93 as input to a SONAR array processing algorithm within computer processor 94 to determine the sub-bubble-resonant speed of sound. First pressure transducer 91 and second pressure transducer 92 can comprise acoustic pressure sensors. It should be noted that for the purposes of this disclosure, first pressure transducer 91 and second pressure transducer 92 and SONAR array processing algorithm produce a speed of sound in the acoustic frequency range, and it is referred to herein as an acoustic sound speed of the process fluid. Such acoustic frequencies are frequencies for which the wavelength of sound propagating through the process fluid is at least greater than the characteristic dimension of the conduit in which the fluid is being conveyed. These acoustic frequencies are associated with acoustics that are essentially one-dimensional acoustics waves that propagate within the piping network where the flow conduits essentially serve as waveguides for the acoustic waves. Augmented Coriolis meter 90 further includes a pair of normal incident ultrasonic transmitter 95 and receiver 96 deployed across the diameter of the conduit 97 containing the process fluid to measure the super-bubble-resonant sound speed. Coriolis meter 93 is configured to flow a process fluid therethrough and includes transmitter 98 which is used to calculate and report the apparent mass flow and density of the process fluid to computer processor 94. The apparent mass flow and density is defined as the mass and flow density reported by a Coriolis meter calibrated on a homogenous fluid of low or negligible reduced frequency. It is noted that there are many other embodiments that could be utilized to implement the methodology described within this disclosure. For example, the sub-bubble-resonant sound speed measurement could be made with clamp-on strain sensors attached to the flow tubes 99 of the Coriolis meter 93, or, for example, the super-bubble-resonant sound speed measurement could be made with non-normal incident ultrasonic transducers.

Figure 10:
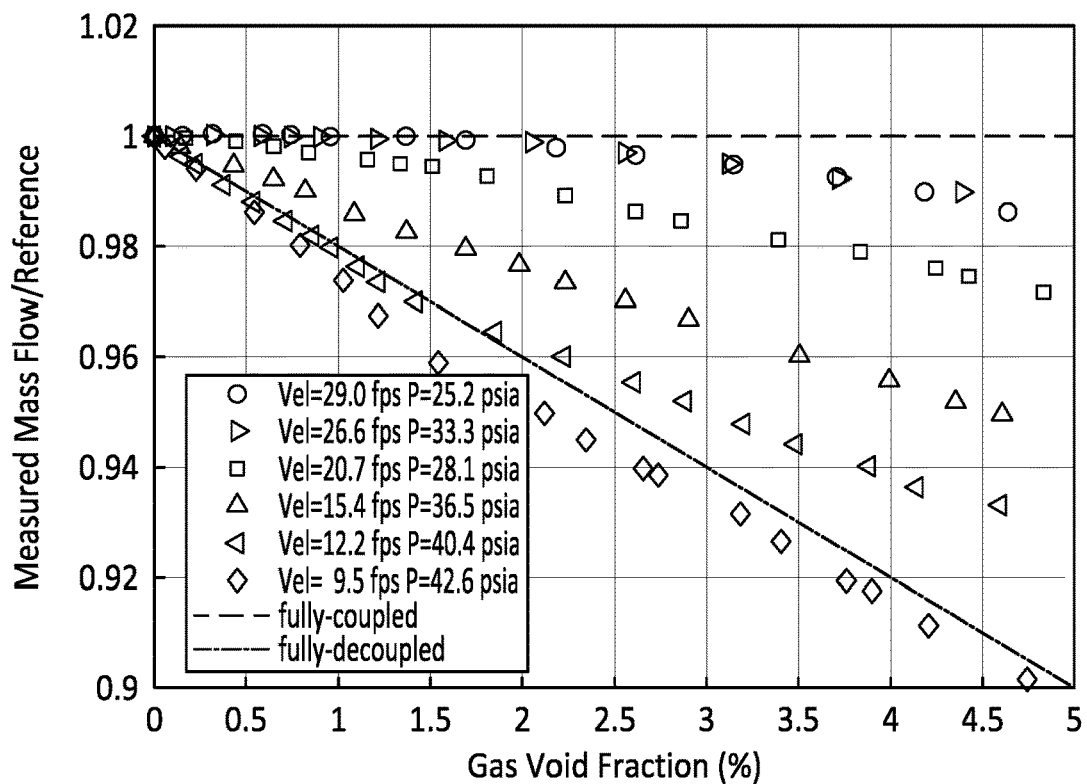
FIG. 10 is a graphical representation of the mass flow rate versus gas void fraction of a Coriolis meter in accordance with the present disclosure.
Figure 11:
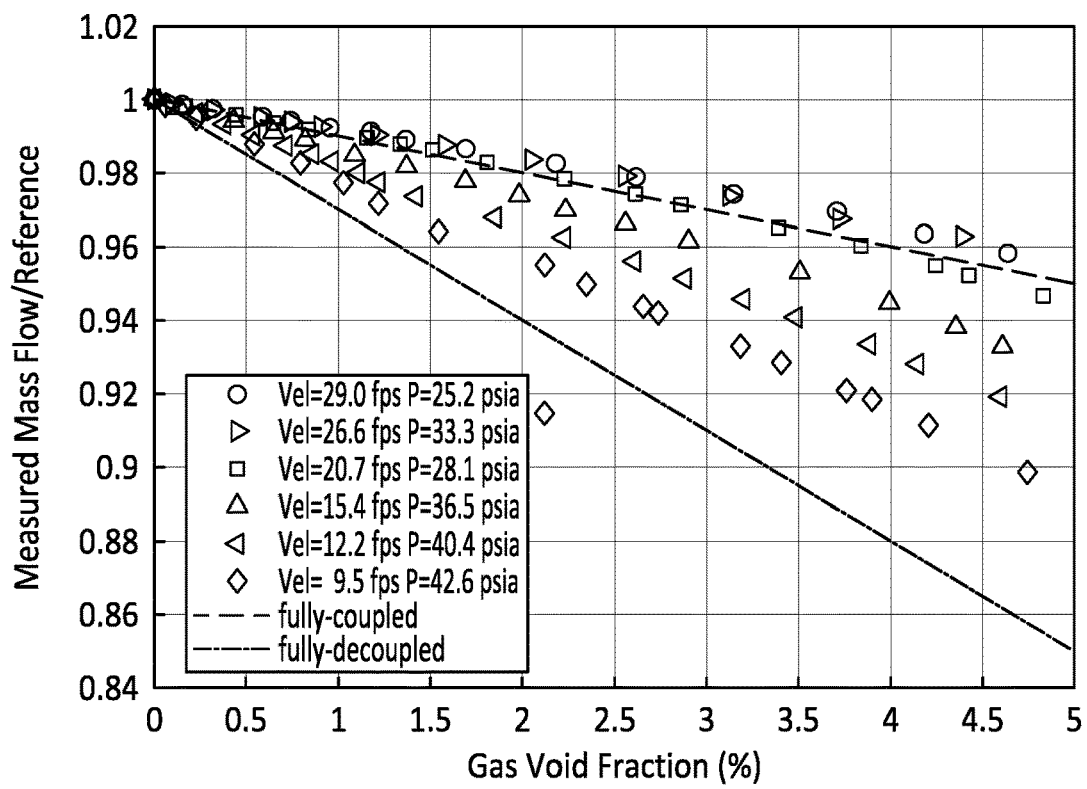
FIG. 11 is a graphical representation of the liquid density versus gas void fraction of a Coriolis meter in accordance with the present disclosure.
Figure 12:
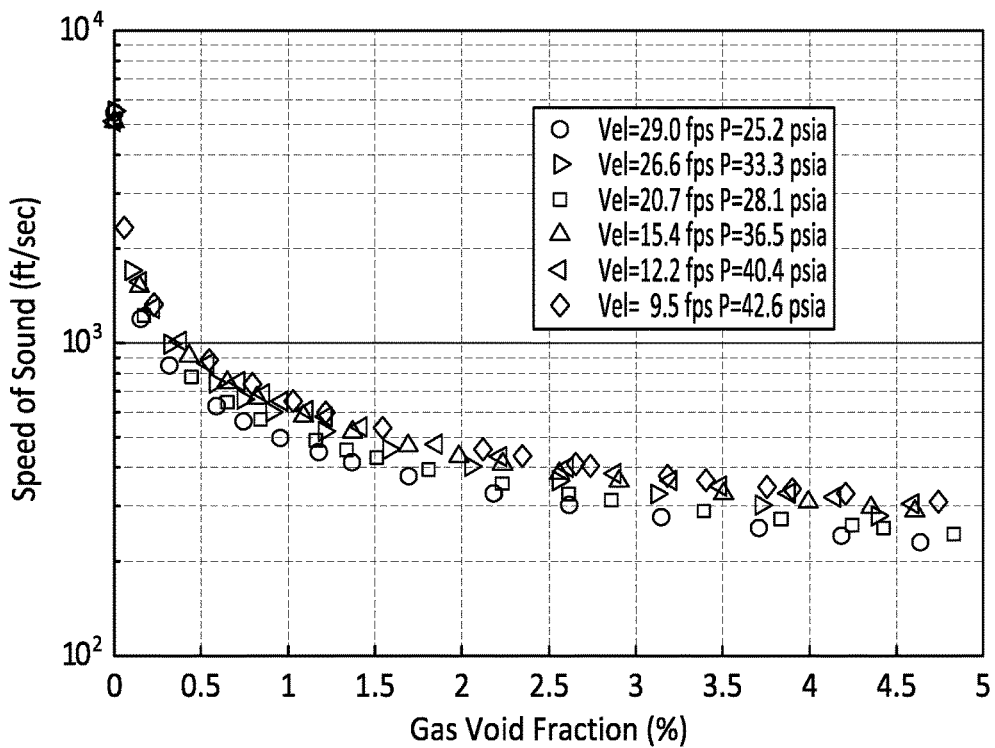
FIG. 12 is a graphical representation of the speed of sound in a bubbly mixture versus gas void fraction of a Coriolis meter in accordance with the present disclosure.

Referring to FIGS. 10-11, there is shown the measured mass flow (normalized by the reference liquid mass flow) and the measured density (normalized by the liquid density) for a Coriolis meter operating on bubbly air/water mixtures over a range of pressure, at nominal mixture flow rates, and gas void fractions. The graphs show the ratio between measured liquid mass flow and reference liquid mass flow as a function of gas void fraction, and measured liquid density and reference liquid density for a Coriolis meter operating on bubbly mixtures of air and water over a range of gas void fractions and nominal flow rates. It should be noted that the process fluid sound speed data for each point was measured as well. Referring next to FIG. 12, there is shown the measured sub-bubble-resonant sound speed for each of the data points shown. An optimization procedure 130 for determining optimal compressibility error coefficients $G_m$ and $G_d$ respectively, can be seen with reference to FIG. 13. Optimization procedure 130 can be used to determine optimized values for the compressibility constants used in the definition of the non-dimensional density decoupling error term and the non-dimensional mass flow decoupling error term as well as an optimized low order polynomial curve fit for the correlation. Using a set of reference data for which and the measured and reference mass flow, density, sub-bubble-resonant sound speed are known for multiple operating conditions, along with other parameters of the Coriolis meter such as tube vibrational frequency and the flow tube diameter, an optimized set of compressibility error coefficients ($G_m$ and $G_d$) can be determined based on an optimization process 130 that maximizes the coefficient of determination of a curve fit of the $\Phi^*$ function versus $\Psi^*$ function. It should be noted here that the objective of the optimization function is to determine an optimized set of compressibility error coefficients ($G_m$ and $G_d$) which maximize the coefficient of determination of the low order curve fit between the mass flow decoupling error term and the density decoupling error term.

Figure 14:
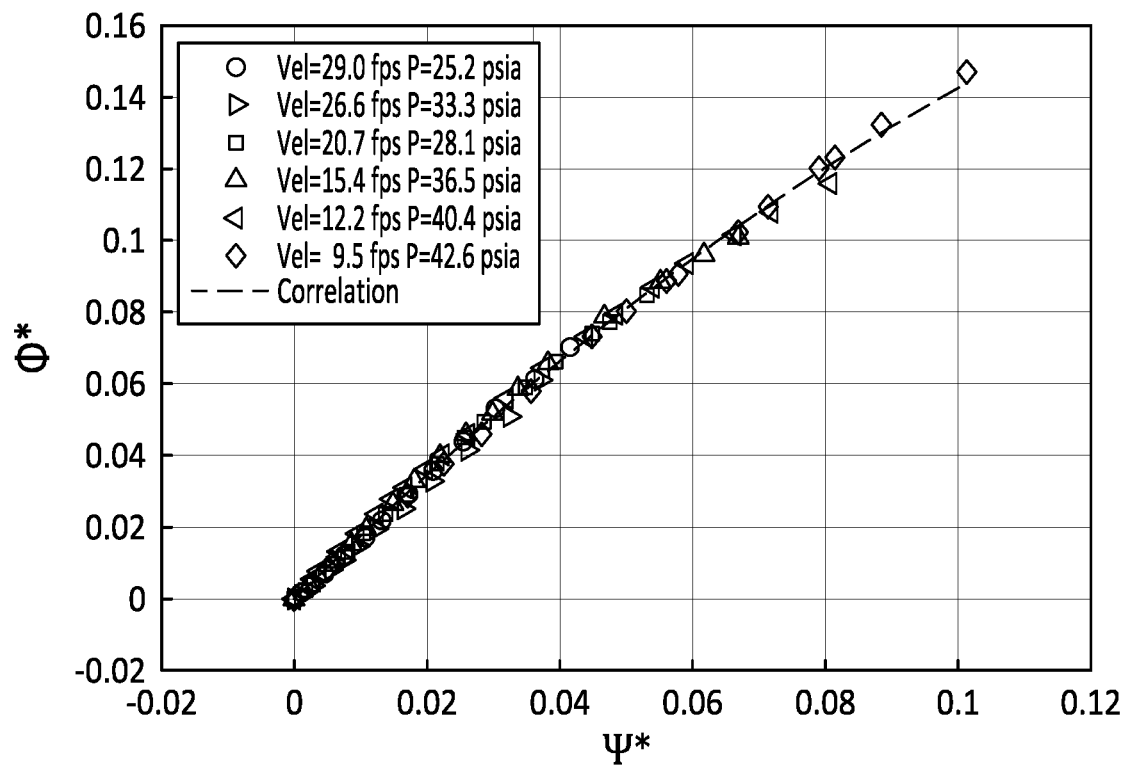
FIG. 14 is a graphical representation of an optimized mass flow decoupling error term versus an optimized density decoupling error term in accordance with the present disclosure.

Referring now to FIG. 14, there is shown the optimized mass flow decoupling error term $\Phi^*$ versus the optimized density decoupling error term $\Psi^*$ for the data presented above. For this data set, the optimized density compressibility constant is Gd=−0.01 and the optimized mass flow compressibility constant is Gm=0.81. A second order polynomial fit of the correlation function is given by:

$$\Phi^*(\Psi^*)=-3.96*\Psi^{*2}+1.83*\Psi^*+0.0 \quad \text{(Equation 4)}$$

The coefficient of determination for this fit is R^2=0.998, indicating that the mass flow decoupling error term, $\Phi^*$, is highly correlated with the density decoupling term, $\Psi^*$. For any given operating point for which the density of the liquid phase is known, as well as the sub-bubble-resonant sound speed, and the optimized density compressibility term is known, the density decoupling error term, $\Psi^*$, can be calculated. With $\Psi^*$ known, the mass flow decoupling error, $\Phi^*$, can be determined.

Figure 13:
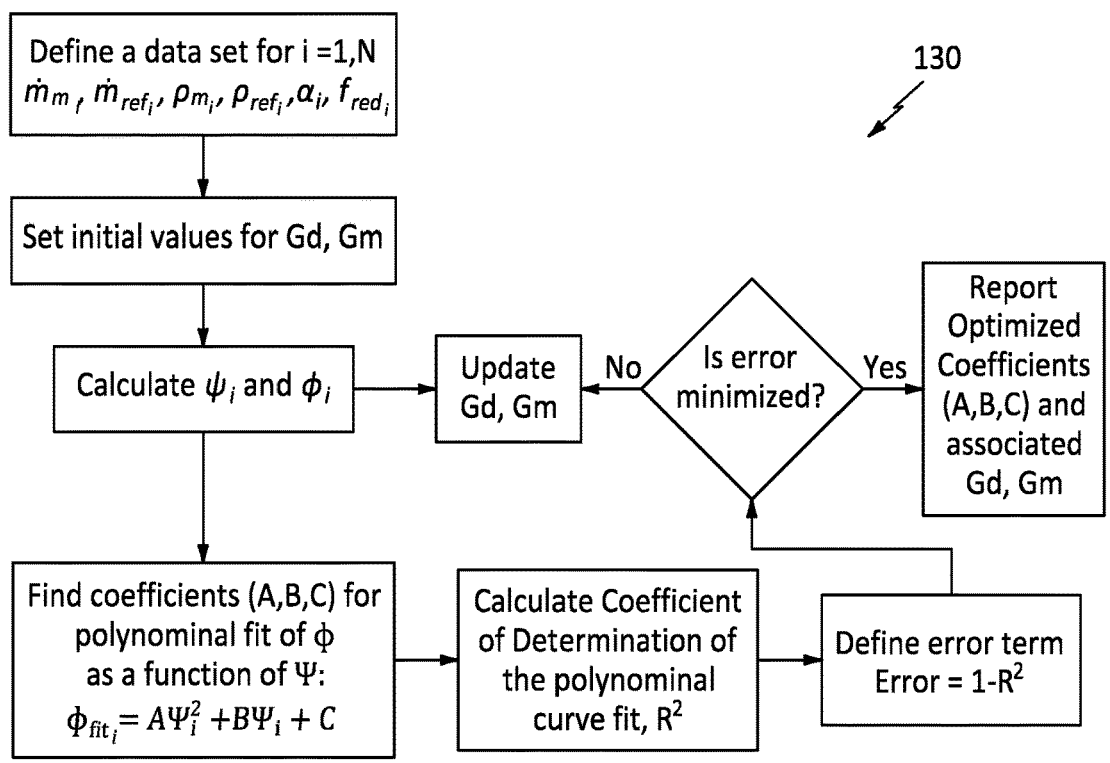
FIG. 13 is a schematic representation of an optimization procedure in accordance with the present disclosure.
Figure 15:
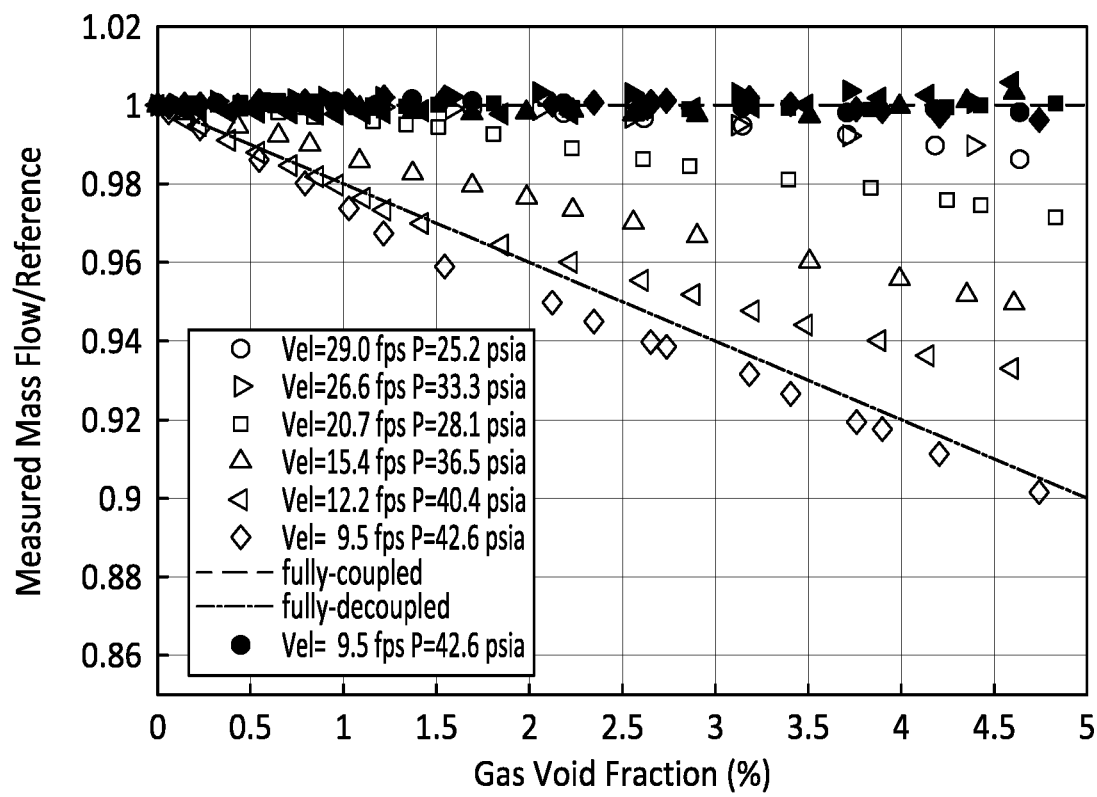
FIG. 15 is a graphical representation a measured flow and corrected mass flow in accordance with the present disclosure.

With $\Phi^*$ determined, a corrected mass flow can be determined using the measured mass flow, the gas void fraction, and the reduced frequency (from the sub-bubble-resonant sound speed) and the known optimized mass flow compressibility constant. FIG. 15 is a graphical representation showing the measured mass flow (as measure by a Coriolis meter) and a corrected mass flow for the data shown above, utilizing the method optimization process 130 (FIG. 13). As shown, the corrected mass flow is in good agreement with the reference mass flow.

Figure 16A:
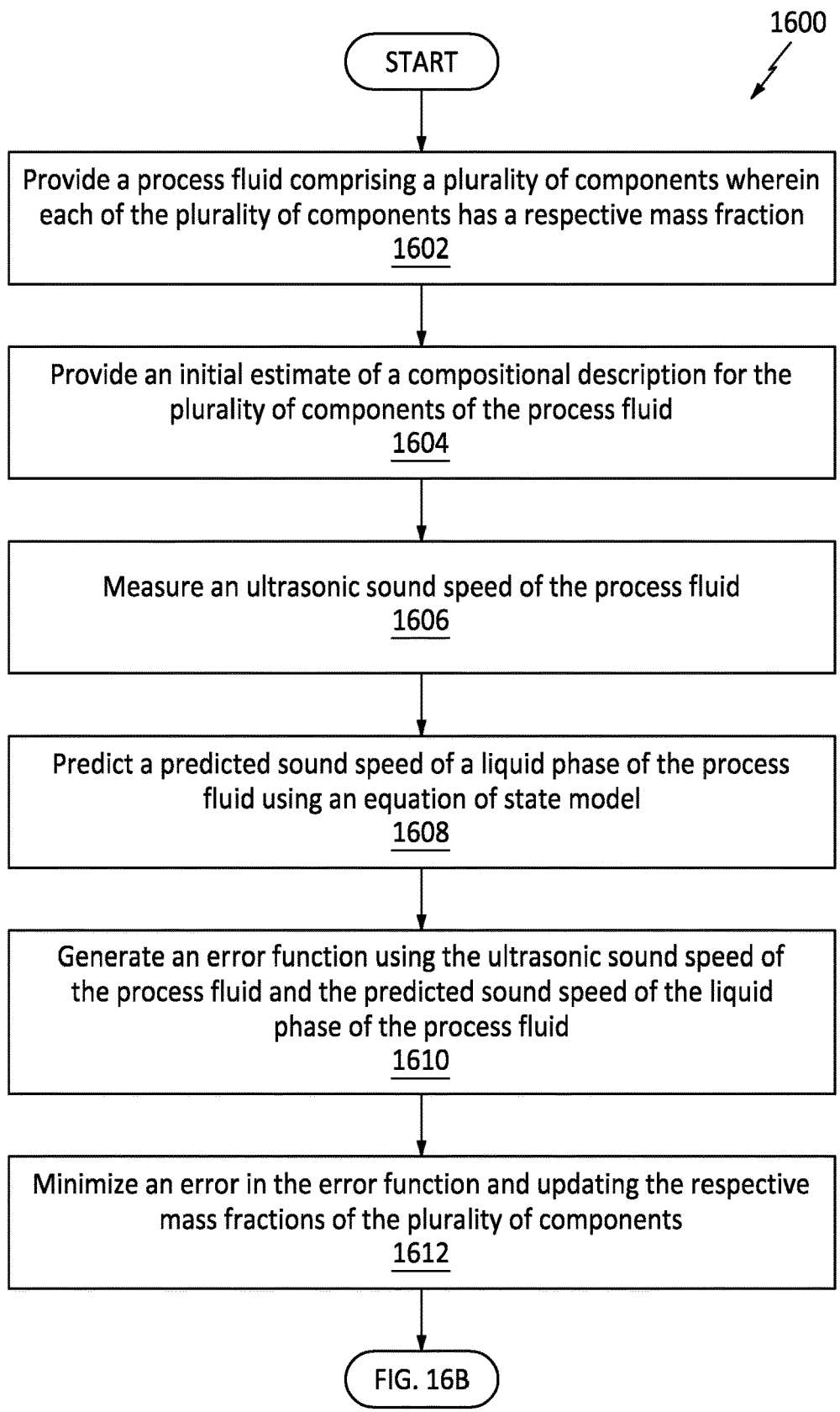
FIG. 16A is a flow chart of implementations of the methods of the current disclosure.
Figure 16B:
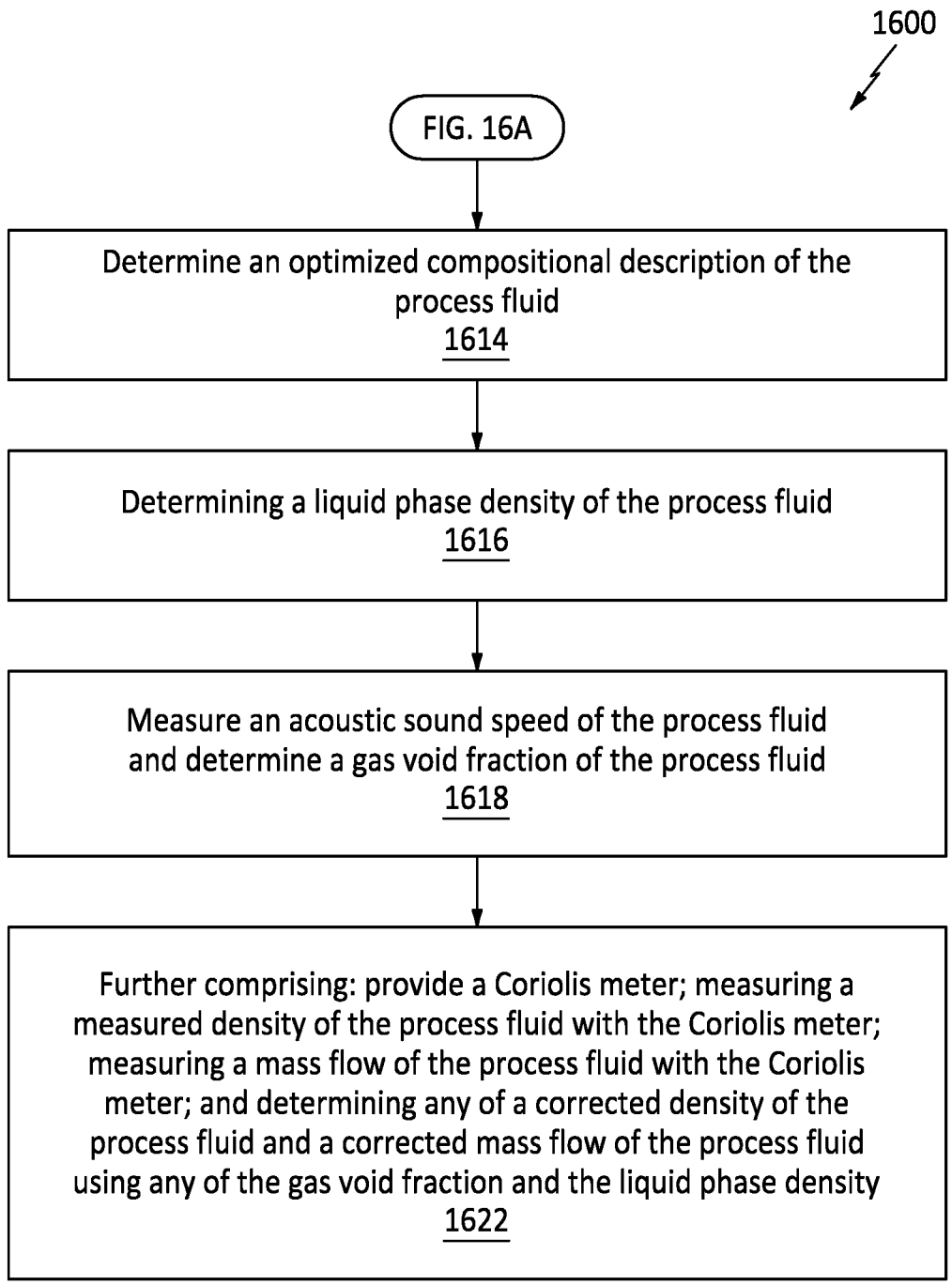
FIG. 16B is a flow chart of implementations of the methods of the current disclosure.

Referring next to FIG. 16, there is shown a flowchart of an example process 1600 in accordance with the present disclosure. In some implementations, one or more process blocks of FIG. 16 may be performed by one or more devices including computer processors.

As shown in FIG. 16, process 1600 may include providing a process fluid having a plurality of components where each of the plurality of components has a respective mass fraction (block 1602). As also shown in FIG. 16, process 1600 may include providing an initial estimate of a compositional description for the plurality of components of the process fluid (block 1604). As further shown in FIG. 16, process 1600 may include measuring an ultrasonic sound speed of the process fluid (block 1606). As also shown in FIG. 16, process 1600 may include predicting a predicted sound speed of a liquid phase of the process fluid using an equation of state model (block 1608). As further shown in FIG. 16, process 1600 may include generating an error function using the ultrasonic sound speed of the process fluid and the predicted sound speed of the liquid phase of the process fluid (block 1610). As also shown in FIG. 16, process 1600 may include minimizing an error in the error function and updating the respective mass fractions of the plurality of components (block 1612). As further shown in FIG. 16, process 1600 may include determining an optimized compositional description of the process fluid (block 1614).

Although FIG. 16 shows example blocks of process 1600, in some implementations, process 1600 may include additional blocks, fewer blocks, different blocks, or differently arranged blocks than those depicted in FIG. 16. Additionally, or alternatively, two or more of the blocks of process 1600 may be performed in parallel.

Operational Example

Figure 17:
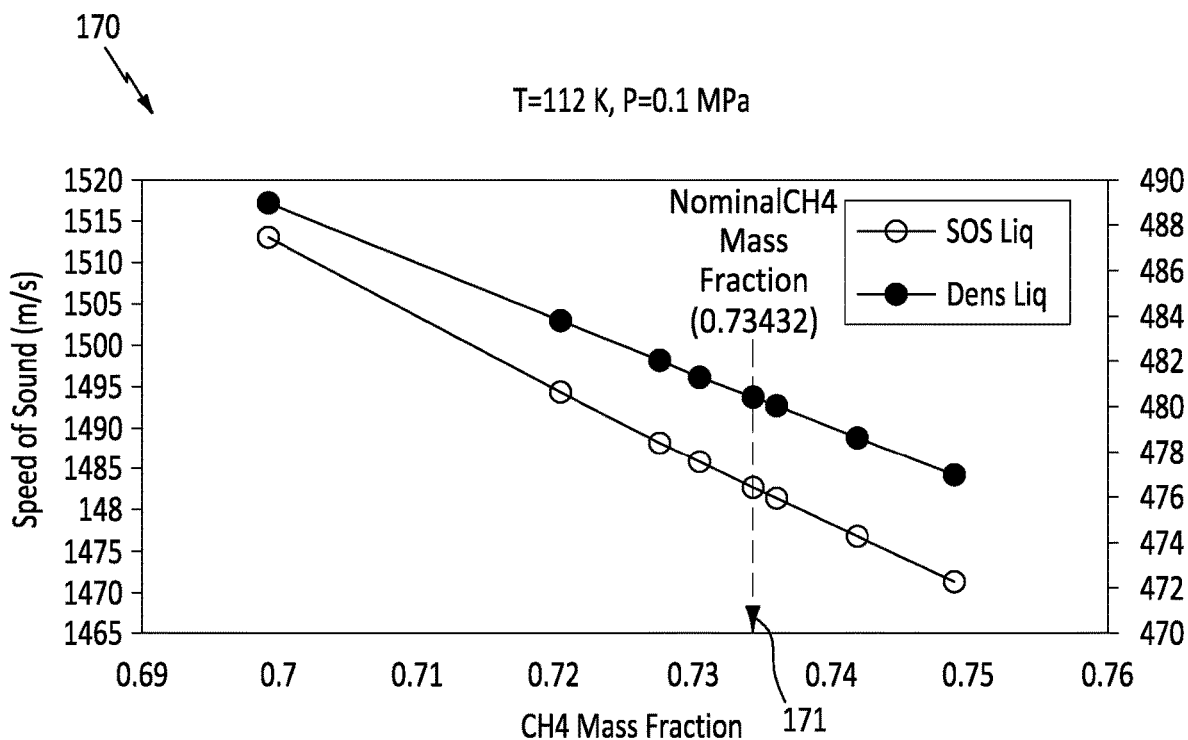
FIG. 17 is a graphical representation of the change in the sound speed and density of a liquid phase of sub-cooled LNG gas as a function of the mass fraction of the methane.

Referring next to FIG. 17, there is shown, in graphical form 170, an example of the change in the sound speed and density of a liquid phase of sub-cooled LNG gas as a function of the mass fraction of the methane for example representative compositions provided in REFPROPS (referenced herein above) at a fixed pressure and temperature. For this calculation, the nominal mass fraction composition 171 was used as starting point with a mass fraction of methane of 73.432%. The mass fraction percent of methane was varied from this nominal condition, with the relative composition of the other components adjusted accordingly to model changes in the methane composition. As shown in FIG. 17, relatively small changes in the mass fraction of the methane result in significant changes in the speed of sound and density of the liquid phase.

One example of a procedure to determine an optimized compositional description of the process fluid of the present disclosure, would be to utilize an initial compositional description to generate a predicted speed of sound at a measured pressure and temperature. This predicted liquid phase sound speed can then be compared to a measured sound speed of the liquid phase to generate an error function. The mass fraction of the methane component of the mixture can then be optimized to minimize the error function. The optimized compositional description can then be used to calculate the density of the liquid phase and other properties of the process fluid utilizing the equation of state model and the optimized composition.

Figure 18:
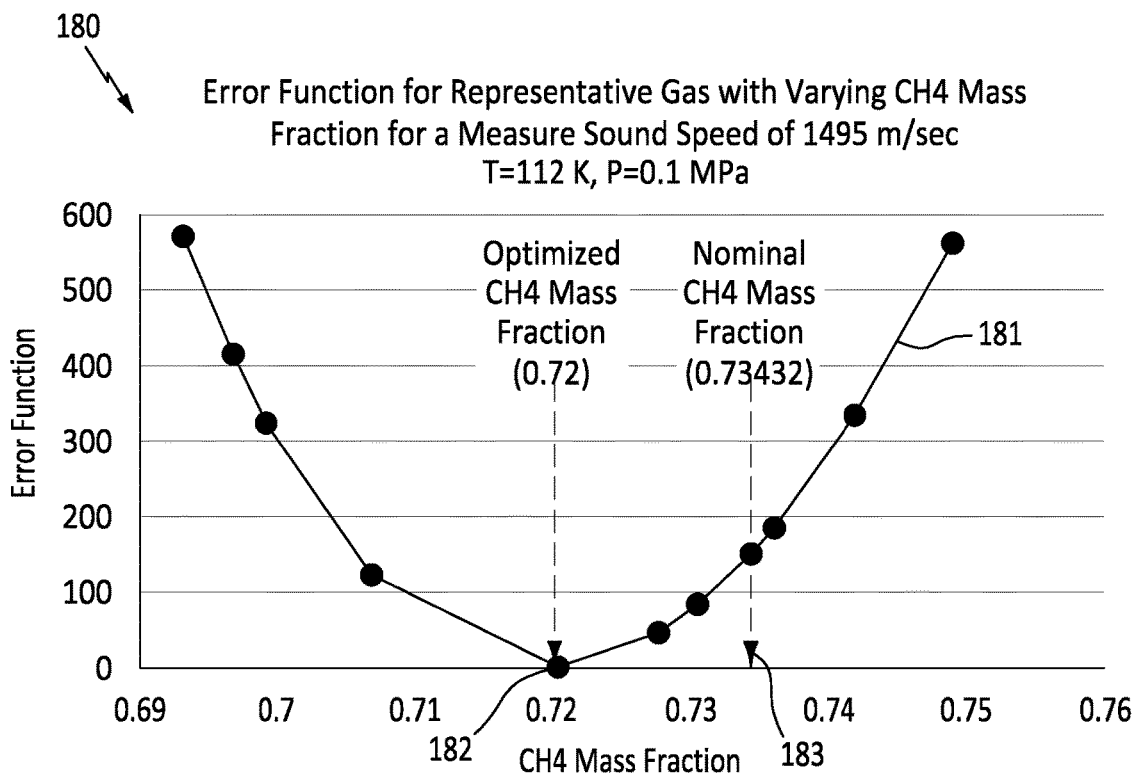
FIG. 18 is a graphical representation of an error function based on the difference between a predicted and a measured sound speed of a liquid phase versus methane mass fraction of a representative natural gas mixture.

An operational example of this optimization process 180 can best be seen with reference to FIG. 18. This process illustrated graphically in FIG. 18 is one in which an error function 181, defined as the square of the difference in measured ultrasonic sound speed and the predicted sound speed of the liquid phase, is plotted versus methane mass fraction for a process fluid having a composition for which the relative mass fractions for all components except for the methane mass fraction are fixed and for which the measured ultrasonic sound speed is 1495 m/sec. As shown the error function 181 is minimized by adjusting the mass fraction of the methane to the optimized mass fraction 182 of 0.72 from the initial estimate 183 of 0.73432. The predicted density of the liquid phase changed from 478.24 kg/m^3 predicted for the initial compositional description at this pressure and temperature, to 483.79 kg/m^3 for the optimized compositional description at this pressure and temperature, a change of ~1.2%, associated with a change in the sound speed of the liquid phase of ~1.7%.

The foregoing disclosure provides illustration and description but is not intended to be exhaustive or to limit the implementations to the precise form disclosed. Modifications may be made in light of the above disclosure or may be acquired from practice of the implementations. As used herein, the term "component" is intended to be broadly construed as hardware, firmware, or a combination of hardware and software. It will be apparent that systems and/or methods described herein may be implemented in different forms of hardware, firmware, and/or a combination of hardware and software. The actual specialized control hardware or software code used to implement these systems and/or methods is not limiting of the implementations. Thus, the operation and behavior of the systems and/or methods are described herein without reference to specific software code—it being understood that software and hardware can be used to implement the systems and/or methods based on the description herein. As used herein, satisfying a threshold may, depending on the context, refer to a value being greater than the threshold, greater than or equal to the threshold, less than the threshold, less than or equal to the threshold, equal to the threshold, and/or the like, depending on the context. Although particular combinations of features are recited in the claims and/or disclosed in the specification, these combinations are not intended to limit the disclosure of various implementations. In fact, many of these features may be combined in ways not specifically recited in the claims and/or disclosed in the specification.

Although each dependent claim listed below may directly depend on only one claim, the disclosure of various implementations includes each dependent claim in combination with every other claim in the claim set. No element, act, or instruction used herein should be construed as critical or essential unless explicitly described as such. Also, as used herein, the articles "a" and "an" are intended to include one or more items and may be used interchangeably with "one or more." Further, as used herein, the article "the" is intended to include one or more items referenced in connection with the article "the" and may be used interchangeably with "the one or more." Furthermore, as used herein, the term "set" is intended to include one or more items (e.g., related items, unrelated items, a combination of related and unrelated items, and/or the like), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise. Also, as used herein, the term "or" is intended to be inclusive when used in a series and may be used interchangeably with "and/or," unless explicitly stated otherwise (e.g., if used in combination with "either" or "only one of").

What is claimed is:

1. A method comprising:
   providing a process fluid comprising a plurality of components wherein each of the plurality of components has a respective mass fraction;
   providing an initial estimate of a compositional description for at least one of the plurality of components of the process fluid;
   measuring an ultrasonic sound speed of the process fluid;
   predicting a predicted sound speed of a liquid phase of the process fluid using an equation of state model;
   generating an error function using the ultrasonic sound speed of the process fluid and the predicted sound speed of the liquid phase of the process fluid;
   minimizing the error function and updating the respective mass fractions of the plurality of components; and
   determining an optimized compositional description of the process fluid.

2. The method of claim 1 further comprising determining a liquid phase density of the process fluid.

3. The method of claim 2 further comprising measuring an acoustic sound speed of the process fluid.

4. The method of claim 3 further comprising determining a gas void fraction of the process fluid.

5. The method of claim 4 further comprising:
   providing a Coriolis meter;
   measuring a measured density of the process fluid with the Coriolis meter;
   measuring a mass flow of the process fluid with the Coriolis meter; and
   determining any of a corrected density of the process fluid and a corrected mass flow of the process fluid using any of the gas void fraction and the liquid phase density.

6. The method of claim 2 wherein the process fluid is proximate a phase transition boundary.

7. The method of claim 1 further comprising predicting at least one parameter of the process fluid using the optimized compositional description of the process fluid.

8. The method of claim 1 further comprising predicting at least one fluid property for a vapor phase of the process fluid using the optimized compositional description of the process fluid.

9. The method of claim 1 wherein the measuring the ultrasonic sound speed of the process fluid comprises measuring frequencies in a range greater than 20 kilohertz.

10. The method of claim 3 wherein measuring the acoustic sound speed of the process fluid comprises measuring frequencies in a range less than 20 kilohertz.

11. The method of claim 5 further comprising:
    positioning a first acoustic pressure sensor proximate an inlet portion of the Coriolis meter and positioning a second acoustic pressure sensor proximate an outlet portion of the Coriolis meter;
    measuring the acoustic sound speed of the process fluid using the first acoustic pressure sensor and the second acoustic pressure sensor;
    positioning at least one ultrasonic transducer on a conduit positioned proximate the outlet portion of the Coriolis meter; and measuring the ultrasonic sound speed of the process fluid using the at least one ultrasonic transducer.

12. A system comprising:
a process fluid comprising a plurality of components wherein each of the plurality of components has a respective mass fraction;
one or more processors configured to:
provide an initial estimate of a compositional description for the plurality of components of the process fluid;
measure an ultrasonic sound speed of the process fluid;
predict a predicted sound speed of a liquid phase of the process fluid using an equation of state model;
generate an error function using the ultrasonic sound speed of the process fluid and the predicted sound speed of the liquid phase of the process fluid;
minimize the error function and updating the respective mass fractions of the plurality of components; and
determine an optimized compositional description of the process fluid.

13. The system of claim 12, further configured to determine a liquid phase density of the process fluid.

14. The system of claim 13, wherein the process fluid is proximate a phase transition boundary.

15. The system of claim 14, further configured to measure an acoustic sound speed of the process fluid.

16. The system of claim 15, further configured to determine a gas void fraction of the process fluid.

17. The system of claim 16, further comprising:
a Coriolis meter configured to:
measure a measured density of the process fluid;
measure a mass flow of the process fluid; and
wherein the one or more processors is further configured to determine any of a corrected density of the process fluid and a corrected mass flow of the process fluid using any of the gas void fraction and the liquid phase density.

18. The system of claim 17, further comprising:
a first acoustic pressure sensor positioned proximate an inlet portion of the Coriolis meter and a second acoustic pressure sensor positioned proximate an outlet portion of the Coriolis meter;
a conduit positioned proximate the outlet portion of the Coriolis meter;
at least one ultrasonic transducer positioned on the conduit; and
wherein the one or more processors is further configured to determine the ultrasonic sound speed of the process fluid using the at least one ultrasonic transducer and to determine the acoustic sound speed of the process fluid using the first acoustic pressure sensor and the second acoustic pressure sensor.

19. The system of claim 15, wherein measuring the acoustic sound speed of the process fluid comprises measuring frequencies in a range less than 20 kilohertz.

20. The system of claim 12, further comprising predicting at least one parameter of the process fluid using the optimized compositional description of the process fluid.

21. The system of claim 12, further comprising predicting at least one fluid property for a vapor phase of the process fluid using the optimized compositional description of the process fluid.

22. The system of claim 12, wherein the measuring the ultrasonic sound speed of the process fluid comprises measuring frequencies in a range greater than 20 kilohertz.

* * * * *